(12) United States Patent
Kobayashi

(10) Patent No.: US 10,705,080 B2
(45) Date of Patent: Jul. 7, 2020

(54) SENSOR APPARATUS

(71) Applicant: KYOCERA CORPORATION, Kyoto (JP)

(72) Inventor: Kyohei Kobayashi, Kyoto (JP)

(73) Assignee: KYOCERA CORPORATION, Kyoto (JP)

( * ) Notice: Subject to any disclaimer, the term of this patent is extended or adjusted under 35 U.S.C. 154(b) by 0 days.

(21) Appl. No.: 15/305,761

(22) PCT Filed: Sep. 30, 2015

(86) PCT No.: PCT/JP2015/077877
§ 371 (c)(1),
(2) Date: Oct. 21, 2016

(87) PCT Pub. No.: WO2016/052679
PCT Pub. Date: Apr. 7, 2016

(65) Prior Publication Data
US 2017/0199180 A1    Jul. 13, 2017

(30) Foreign Application Priority Data

Sep. 30, 2014   (JP) .................................. 2014-201249

(51) Int. Cl.
*G01N 33/543*   (2006.01)
*H03H 9/145*   (2006.01)
(Continued)

(52) U.S. Cl.
CPC ....... *G01N 33/5438* (2013.01); *G01N 29/022* (2013.01); *G01N 29/222* (2013.01);
(Continued)

(58) Field of Classification Search
CPC ............. G01N 33/5438; G01N 29/022; G01N 29/2443; H01L 41/047; H01L 41/1132; H03H 9/145
See application file for complete search history.

(56) References Cited

U.S. PATENT DOCUMENTS 3,831,115 A * 8/1974 Coldren .................... H03H 9/42
                                                    333/150
5,130,257 A    7/1992 Baer et al.
(Continued)

FOREIGN PATENT DOCUMENTS

CN    102484466 A    5/2012
JP    A 55-80912    6/1980
(Continued)

OTHER PUBLICATIONS

International Search Report in International Application No. PCT/JP2015/077877, dated Dec. 22, 2015, in 2 pages.
(Continued)

*Primary Examiner* — Robert J Eom
(74) *Attorney, Agent, or Firm* — Duane Morris LLP

(57) ABSTRACT

A sensor apparatus capable of measuring an analyte with excellent sensitivity is provided. A sensor apparatus includes an element substrate; a detecting section disposed on an upper surface of the element substrate, the detecting element including a reaction section having an immobilization film to detect an analyte, a first IDT electrode configured to generate an acoustic wave which propagates toward the reaction section, and a second IDT electrode configured to receive the acoustic wave which has passed through the reaction section; and a protective film which covers the first IDT electrode and the second IDT electrode. The element substrate is configured so that a region where the reaction section is located is at a lower level than a region where the
(Continued)

first IDT electrode is located and a region where the second IDT electrode is located.

17 Claims, 7 Drawing Sheets

(51) Int. Cl.
    *G01N 29/22* (2006.01)
    *G01N 29/24* (2006.01)
    *G01N 29/02* (2006.01)
    *H01L 41/047* (2006.01)
    *H01L 41/113* (2006.01)

(52) U.S. Cl.
    CPC ..... *G01N 29/2443* (2013.01); *G01N 29/2462* (2013.01); *H01L 41/047* (2013.01); *H01L 41/1132* (2013.01); *H03H 9/145* (2013.01); *G01N 2291/0255* (2013.01)

(56) References Cited

U.S. PATENT DOCUMENTS

| | | | |
|---|---|---|---|
| 5,283,037 A | 2/1994 | Baer et al. | |
| 5,306,644 A | 4/1994 | Myerholtz et al. | |
| 5,321,331 A * | 6/1994 | Baer | G01N 29/022 |
| | | | 310/313 B |
| 6,235,488 B1 | 5/2001 | Tom-moy et al. | |
| 6,626,026 B2 * | 9/2003 | Banda | G01N 29/02 |
| | | | 73/24.01 |
| 2001/0054305 A1 | 12/2001 | Banda et al. | |
| 2002/0192718 A1 | 12/2002 | Tom-moy et al. | |
| 2007/0220986 A1 * | 9/2007 | Smith | B60C 23/0408 |
| | | | 73/727 |
| 2012/0146457 A1 | 6/2012 | Goto et al. | |

FOREIGN PATENT DOCUMENTS

| | | |
|---|---|---|
| JP | A 5-240762 | 9/1993 |
| JP | 6-43016 A | 2/1994 |
| JP | A 2006-184011 | 7/2006 |
| JP | A 2007-10378 | 1/2007 |
| JP | A 2010-239477 | 10/2010 |
| JP | 2014-9955 A | 1/2014 |
| WO | 2011/030519 A1 | 3/2011 |
| WO | 2013/108608 A1 | 7/2013 |

OTHER PUBLICATIONS

Dazhong, Z. et al., "A RF mass-sensitive SAW sensor with U-groove structure", IEEE Antennas and Propagation Society International Symposium, Jul. 8, 2001, pp. 350-353.

* cited by examiner (a)

(b)

SENSOR APPARATUS

TECHNICAL FIELD

The present invention relates to a sensor apparatus which is capable of measurement on the properties or constituents of an analyte liquid.

BACKGROUND ART

There is known a sensor apparatus which measures the properties or constituents of an analyte liquid by detecting an object to be detected contained in the analyte liquid with use of a detecting element such as a surface acoustic wave device (refer to Patent Literatures 1 to 3, for example).

For example, in a sensor apparatus employing a surface acoustic wave device, a reaction section which undergoes reaction with a component contained in a sample of an analyte liquid, is disposed on a piezoelectric substrate, and the properties or constituents of the analyte liquid are detected by measuring variation in a surface acoustic wave propagating through the reaction section. Such a measurement method using the surface acoustic wave device or the like has the advantage over other measurement methods (for example, enzymatic method) in that it lends itself to simultaneous detection of a plurality of characteristics to be measured.

However, in such a conventional sensor apparatus, since the reaction section, which is placed between a pair of IDT electrodes, is not positioned at a level which is sufficiently low relative to the IDT electrodes, it follows that surface-acoustic-wave energy cannot be readily concentrated on the reaction section, which leads to difficulties in detecting an object to be detected contained in the analyte liquid with high sensitivity.

CITATION LIST

Patent Literature

Patent Literature 1: Japanese Unexamined Patent Publication JP-A 5-240762 (1993)
Patent Literature 2: Japanese Unexamined Patent Publication JP-A 2006-184011
Patent Literature 3: Japanese Unexamined Patent Publication JP-A 2010-239477

SUMMARY OF INVENTION

Technical Problem

Thus, there is a demand for a sensor apparatus which is capable of detecting an object to be detected contained in an analyte liquid with excellent sensitivity.

Solution to Problem

A sensor apparatus according to an embodiment of the invention includes: an element substrate; a detecting section disposed on an upper surface of the element substrate, the detecting section including a reaction section having an immobilization film to detect an object to be detected, a first IDT electrode configured to generate an acoustic wave which propagates toward the reaction section, and a second IDT electrode configured to receive the acoustic wave which has passed through the reaction section; and a protective film which covers the first IDT electrode and the second IDT electrode, wherein the upper surface of the element substrate is configured so that a region where the reaction section is located is at a lower level than a region where the first IDT electrode is located and a region where the second IDT electrode is located.

Advantageous Effects of Invention

In accordance with the sensor apparatus according to the embodiment of the invention, the upper surface of the element substrate is configured so that the region where the reaction section is located is at a lower level than the region where the first IDT electrode and the second IDT electrode are located. Therefore, in the reaction section, energy of the surface acoustic wave propagating between the first IDT electrode and the second IDT electrode is readily concentrated on the immobilization film, measurement can be carried out with high sensitivity.

BRIEF DESCRIPTION OF DRAWINGS

FIG. 1(a) is a plan view,
FIG. 1(b) is a lengthwise sectional view,
and FIG. 1(c) is a widthwise sectional view.

DESCRIPTION OF EMBODIMENTS

Hereinafter, embodiments of a sensor apparatus according to the invention will be described with reference to drawings. In each drawing to be referred to in the following description, like constituent members are identified with the same reference symbols. Moreover, for example, the size of each member and the distance between the individual members are schematically shown in each drawing and may therefore differ from the actual measurements.

<Structure of Sensor Apparatus>

Figure 1:
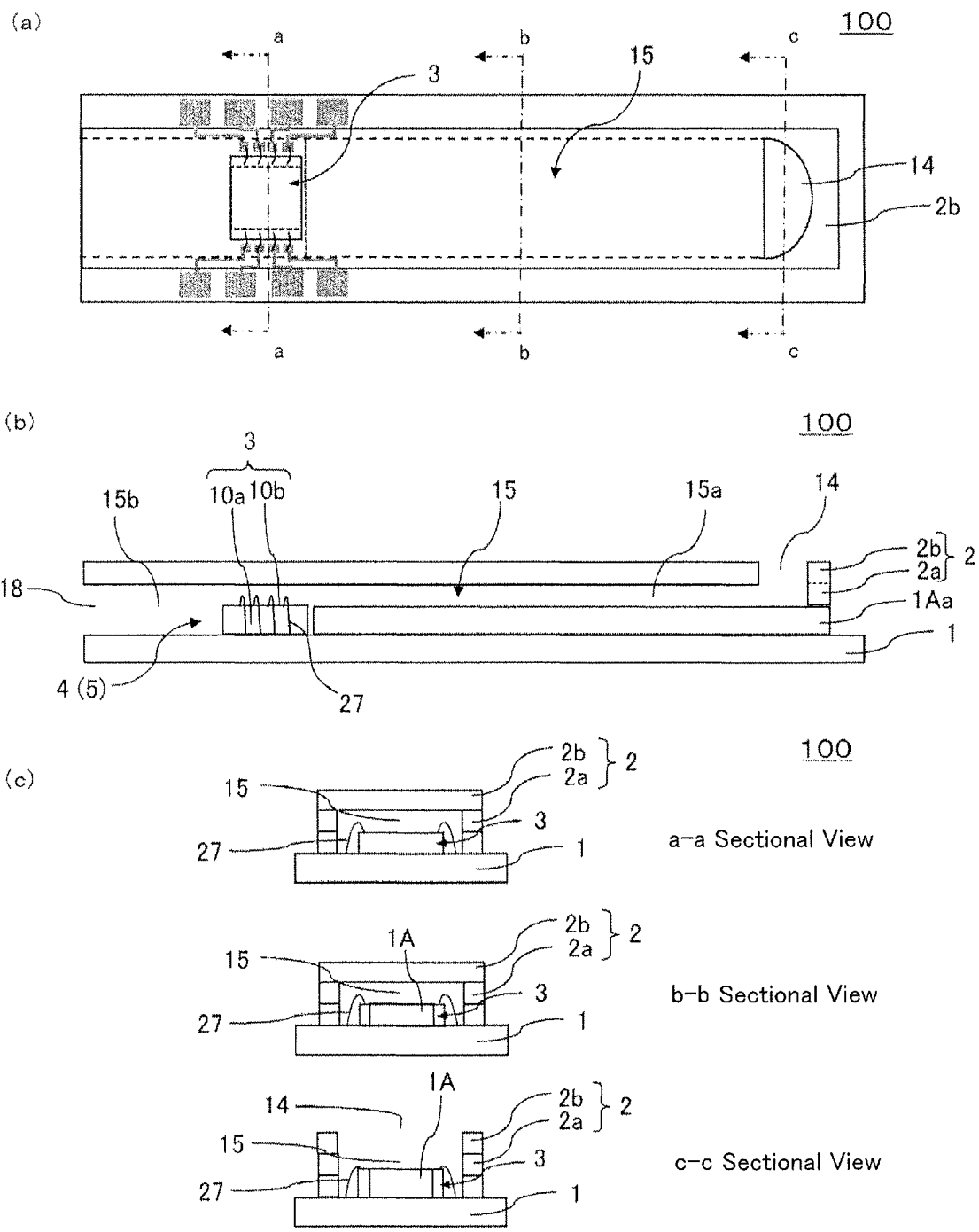
FIG. 1 is a view showing a sensor apparatus according to an embodiment of the invention.

A sensor apparatus 100 according to an embodiment of the invention will be described with reference to FIGS. 1 to 6. As shown in FIG. 1, the sensor apparatus 100 according to the embodiment mainly comprises a first cover member 1, an intermediate cover member 1A, a second cover member 2, and a detecting element 3.

Specifically, as shown in FIG. 1(b), the sensor apparatus 100 has an inlet port 14 for admission of an analyte liquid, and a flow channel 15 which is in communication with the inlet port 14, is surrounded by the intermediate cover member 1A and the second cover member 2, and extends at least to a reaction section 13. In this embodiment, the intermediate cover member 1A and the second cover member 2 are greater in width than the detecting element 3. This allows an analyte liquid to flow so as to cover the entire surface of the detecting element 3 effectively.

FIG. 1(c) which shows sectional views of the construction shown in FIG. 1(a), wherein there are successively shown, in top-to-bottom order, a section taken along the line a-a, a section taken along the line b-b, and a section taken along the line c-c. The inlet port 14 is formed so as to pass through the second cover member 2 in a thickness direction thereof.

(First Cover Member 1)

Figure 2:
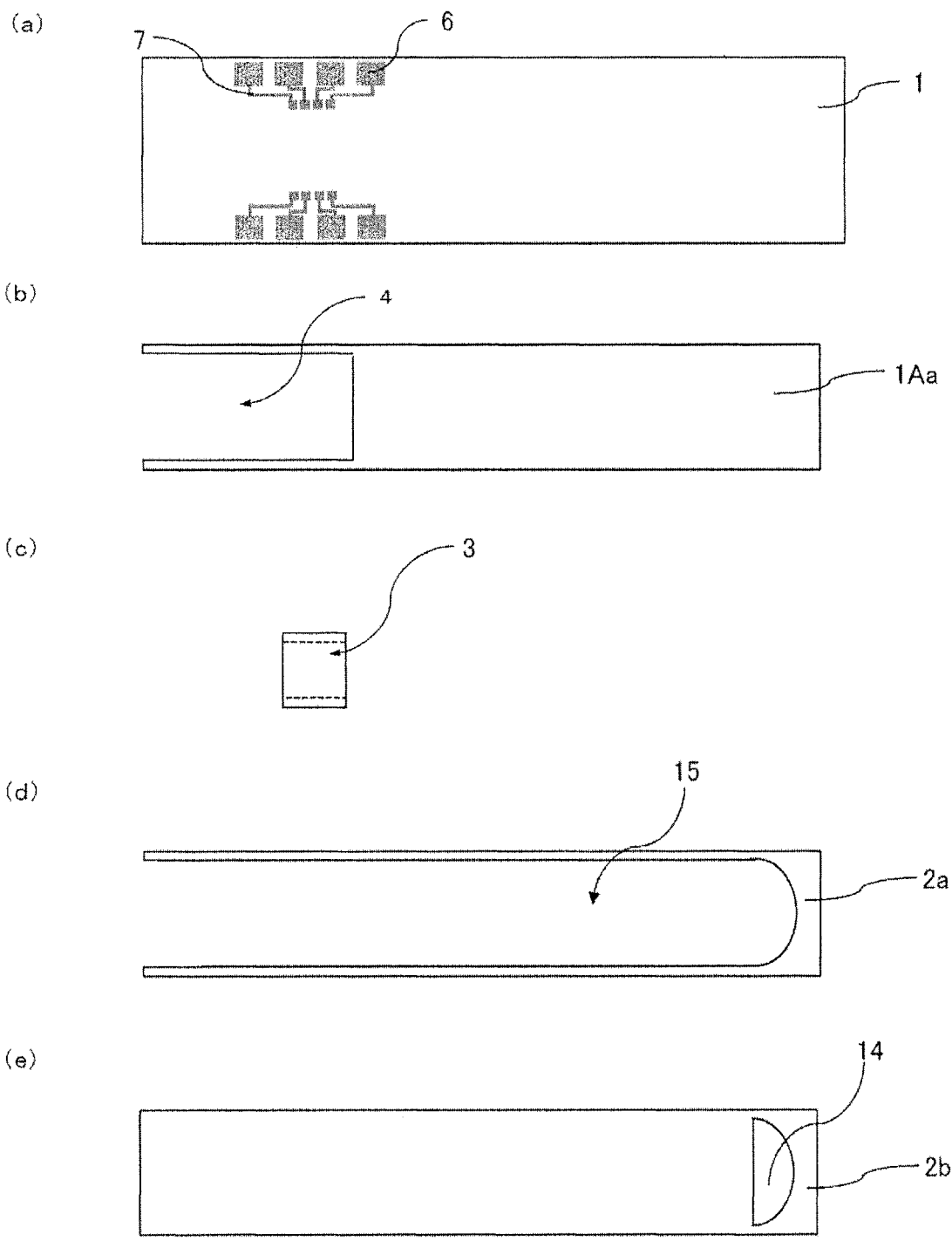
FIG. 2 is an exploded plan view of the sensor apparatus shown in FIG. 1.

As shown in FIGS. 1(*a*), 1(*b*) and FIG. 2(*a*), the first cover member 1 is shaped like a flat plate. The thickness of the first cover member 1 falls in the range of 0.1 mm to 1.5 mm, for example. The first cover member 1 has substantially a rectangular planar configuration. The longitudinal length of the first cover member 1 falls in the range of 1 cm to 8 cm, for example, and, the widthwise length of the first cover member 1 falls in the range of 1 cm to 3 cm, for example.

As the material for forming the first cover member 1, for example, a glass-epoxy material, paper, plastics, celluloid, ceramics, non-woven fabric, and glass can be used. The use of plastics is desirable from the standpoints of required strength and cost.

Moreover, as shown in FIGS. 1(*a*) and 2(*a*), on the upper surface of the first cover member 1 are formed a terminal 6 and a wiring line 7 routed from the terminal 6 to a position near the detecting element 3.

Figure 4:
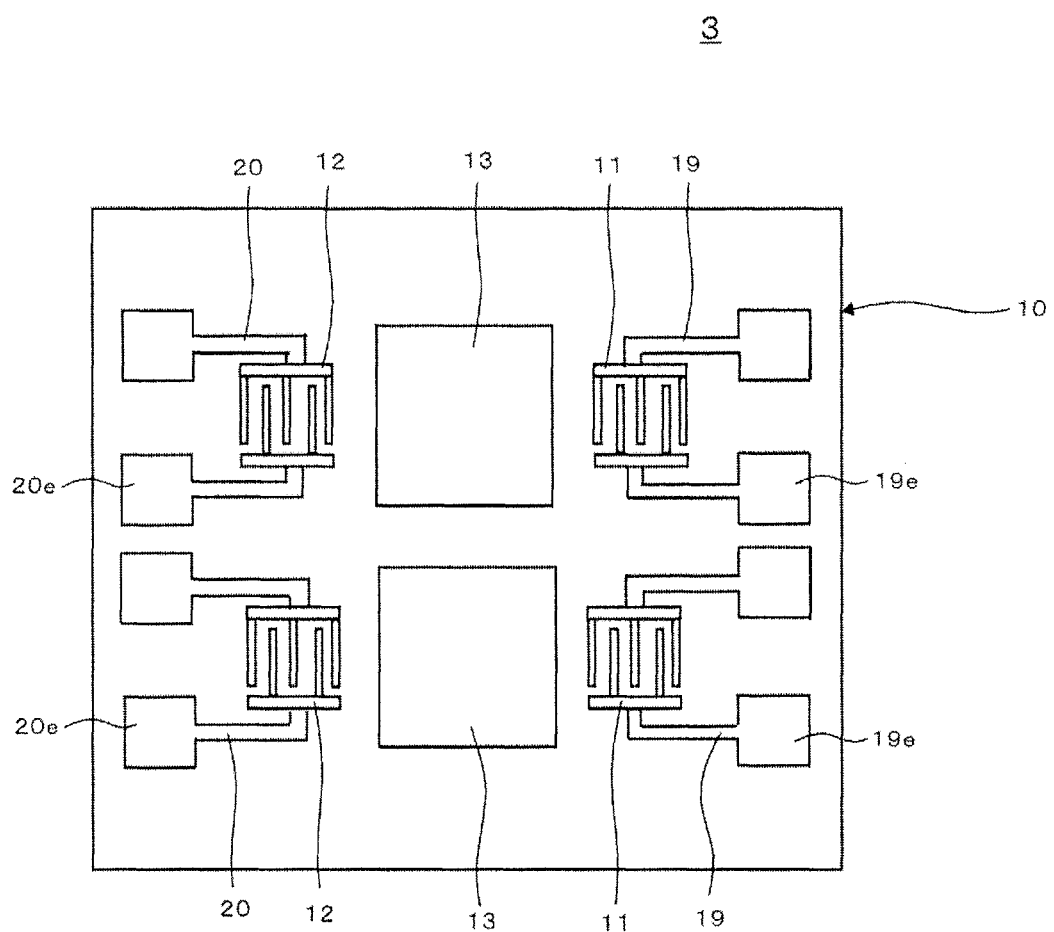
FIG. 4 is a plan view showing a detecting element of the sensor apparatus shown in FIG. 1.

The terminal 6 is formed on either side of the detecting element 3 in a width direction on the upper surface of the intermediate cover member 1A. Specifically, at least part of the terminals 6 arranged relative to the detecting element 3 lies closer to the inlet port 14 than an inlet port 14-side end of the detecting element 3. Moreover, in the range of four terminals 6 placed in an array on one side of the detecting element 3 with respect to a direction longitudinally of the flow channel 15, the wiring lines 7 connected to two outer terminals 6, respectively, have substantially the same length, and, the wiring lines 7 connected to the other two inner terminals 6, respectively, have substantially the same length. This makes it possible to reduce variations in signals obtained by the detecting element 3 resulting from the difference in length between the wiring lines 7. In this case, with a construction in which the wiring lines 7 are connected so that a potential difference occurs between grounding (earthing) wiring, which is constituted by one pair of the wiring lines 7 having substantially the same length, and signal wiring, which is constituted by the other pair of the wiring lines 7 having substantially the same length, for example, upon application of a predetermined voltage from external measurement equipment to a first IDT electrode 11 as shown in FIG. 4 via the wiring line 7, a first extraction electrode 19, and so forth, it is possible to reduce the signal variations, and thereby achieve an improvement in detection reliability.

When measurement is made on the sensor apparatus 100 with external measuring equipment (not shown in the drawing), the terminal 6 and the external measuring equipment are electrically connected to each other. Moreover, the terminal 6 and the detecting element 3 are electrically connected to each other via the wiring line 7, for example.

A signal issued from the external measuring equipment is inputted to the sensor apparatus 100 via the terminal 6, and, a signal issued from the sensor apparatus 100 is outputted to the external measuring equipment via the terminal 6.

(Intermediate Cover Member 1A)

In this embodiment, as shown in FIG. 1(*b*), the intermediate cover member 1A is placed in juxtaposition to the detecting element 3 on the upper surface of the first cover member 1. Moreover, as shown in FIGS. 1(*a*) and 3(*c*), the intermediate cover member 1A and the detecting element 3 are arranged with a spacing. Note that the intermediate cover member 1A and the detecting element 3 may be arranged with their sides kept in contact with each other.

As shown in FIGS. 1(*b*) and 2(*b*), the intermediate cover member 1A has the form of a flat frame constructed of a flat plate having a recess-forming area 4, and, the thickness of the intermediate cover member 1A falls in the range of 0.1 mm to 0.5 mm, for example.

In this embodiment, as shown in FIG. 1(*b*), the recess-forming area 4 is an area located downstream of a first upstream portion 1Aa. The intermediate cover member 1A is joined to the flat plate-shaped first cover member 1, whereupon an element placement section 5 is defined by the first cover member 1 and the intermediate cover member 1A. That is, the upper surface of the first cover member 1 located inside the recess-forming area 4 becomes the bottom surface of the element placement section 5, and, the inner wall of the recess-forming area 4 becomes the inner wall of the element placement section 5.

Figure 3:
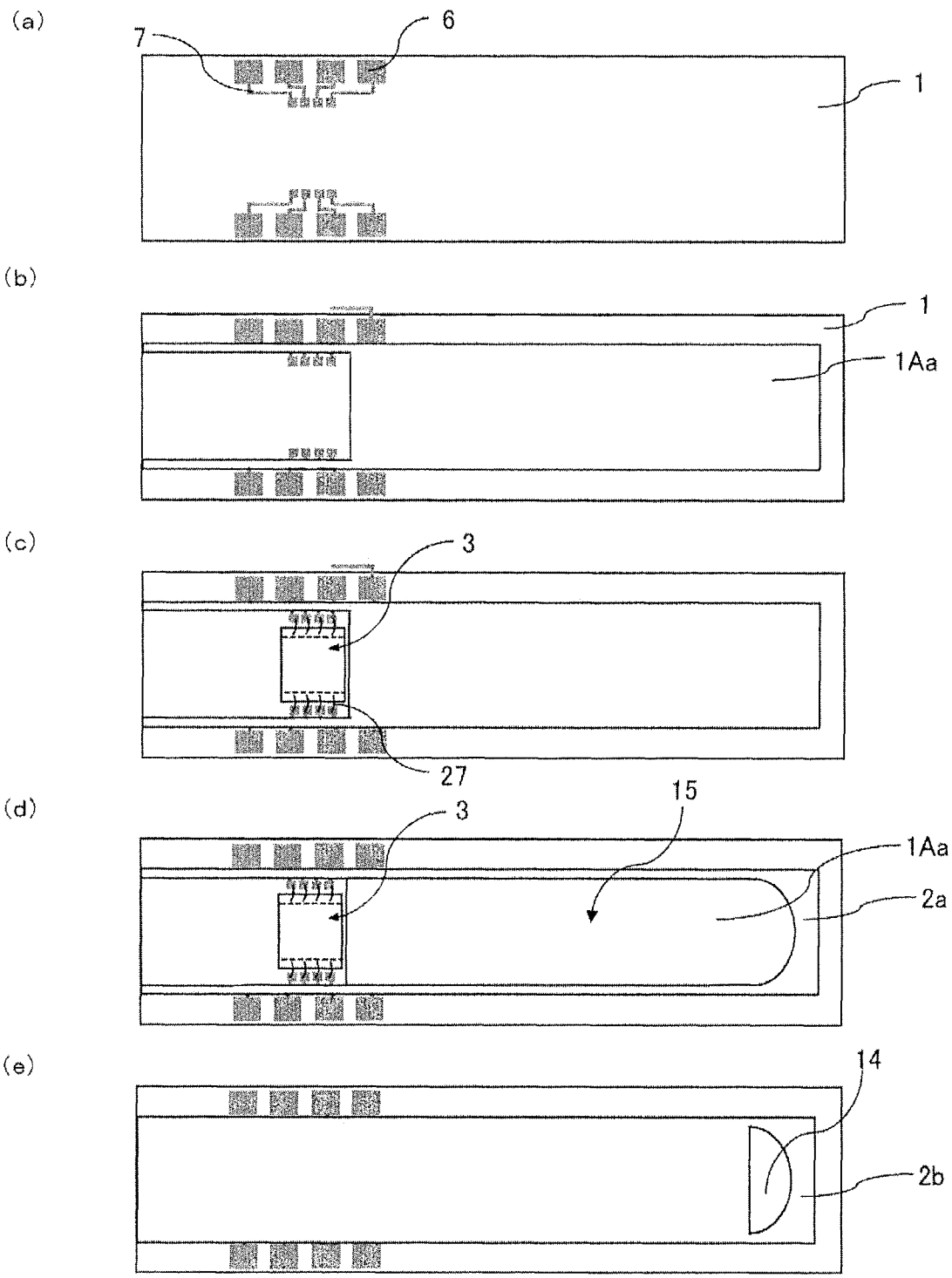
FIG. 3 is a plan view showing procedural steps to manufacture the sensor apparatus shown in FIG. 1.

As shown in FIGS. 1 and 3, in a region located downstream of the detecting element 3, the intermediate cover member 1A does not exist on the first cover member 1. This makes it possible to inhibit or reduce generation of bubbles in a part of the intermediate cover member 1A located downstream of the first upstream portion 1Aa. In consequence, an analyte liquid can be delivered in a bubble-free state onto the detecting element 3, thus achieving an improvement in sensitivity or accuracy in detection.

As the material for forming the intermediate cover member 1A, for example, resin (including plastics), paper, non-woven fabric, and glass can be used. More specifically, resin materials such as polyester resin, polyethylene resin, acrylic resin, and silicone resin are desirable for use. The first cover member 1 and the intermediate cover member 1A may be formed of either the same material or different materials.

Moreover, in this embodiment, the intermediate cover member 1A includes the first upstream portion 1Aa. As shown in FIGS. 1(*a*) and 1(*b*), when viewed from above, the detecting element 3 is located on the downstream side relative to the first upstream portion 1Aa. In this case, when an analyte liquid flows out over the detecting element 3 after passing through a part of the flow channel 15 which corresponds to the first upstream portion 1Aa, an excess of the analyte liquid over an amount of the analyte liquid required for measurement flows downstream, wherefore an adequate amount of the analyte liquid can be fed to the detecting element 3.

(Second Cover Member 2)

As shown in FIGS. 1(*b*) and 3(*e*), the second cover member 2 covers the detecting element 3, and is joined to the first cover member 1 and the intermediate cover member 1A. As shown in FIGS. 1(*b*) and 1(*c*), the second cover member 2 comprises a third substrate 2a and a fourth substrate 2b.

As the material for forming the second cover member 2, for example, resin (including plastics), paper, non-woven fabric, and glass can be used. More specifically, resin materials such as polyester resin, polyethylene resin, acrylic resin, and silicone resin are desirable for use. The first cover member 1 and the second cover member 2 may be formed of the same material. In this case, deformation resulting from the difference in thermal expansion coefficient between the first and second cover members can be minimized. The second cover member 2 may either be joined only to the intermediate cover member 1A or be joined to both of the first cover member 1 and the intermediate cover member 1A.

As shown in FIGS. 1(*c*), 3(*c*), and 3(*d*), the third substrate 2a is bonded to the upper surface of the intermediate cover member 1A. The third substrate 2a is shaped like a flat plate having a thickness of 0.1 mm to 0.5 mm, for example. The fourth substrate 2b is bonded to the upper surface of the third substrate 2a. The fourth substrate 2b is shaped like a flat plate having a thickness of 0.1 mm to 0.5 mm, for example. By joining the fourth substrate 2b to the third substrate 2a, as shown in FIG. 1(b), the flow channel 15 is formed on the lower surface of the second cover member 2. The flow channel 15 extends from the inlet port 14 to at least a region immediately above the reaction section 13, and has a rectangular sectional profile, for example. The third substrate 2a and the fourth substrate 2b may be formed of the same material, or, an unitary construction of the combined third and fourth substrates 2a and 2b may be used.

In this embodiment, as shown in FIG. 1(b), neither the intermediate cover member 1A nor the third substrate 2a exists at an end of the flow channel 15, and, a gap left between the fourth substrate 2b and the first cover member 1 serves as an air release hole 18. The air release hole 18 is provided to let air and so forth present in the flow channel 15 go out. The opening of the air release hole 18 may be given any shape which is capable of release of air present in the flow channel 15, and thus, for example, a circular shape or a rectangular shape may be adopted. For example, a circular air release hole 18 is designed to have a diameter of less than or equal to 2 mm, and, a rectangular air release hole 18 is designed so that each side of it has a length of less than or equal to 2 mm.

The first cover member 1, the intermediate cover member 1A, and the second cover member 2 may be formed of the same material. In this case, since these members are substantially uniform in thermal expansion coefficient, it is possible to reduce deformation of the sensor apparatus 100 caused by the difference in thermal expansion coefficient among the members. Moreover, in the case of application of a biomaterial to the reaction section 13, some biomaterials are prone to quality degradation under external light such as ultraviolet rays. In this regard, it is advisable to use an opaque material having light-blocking capability as the material for forming the first cover member 1, the intermediate cover member 1A, and the second cover member 2. On the other hand, when the reaction section 13 is substantially free of external light-induced quality degradation, the second cover member 2 constituting the flow channel 15 may be formed of a nearly transparent material. In this case, the condition of an analyte liquid flowing through the interior of the flow channel 15 can be visually checked, thus permitting the combined use of an optical detection system.

(Detecting Element 3)

Figure 5:
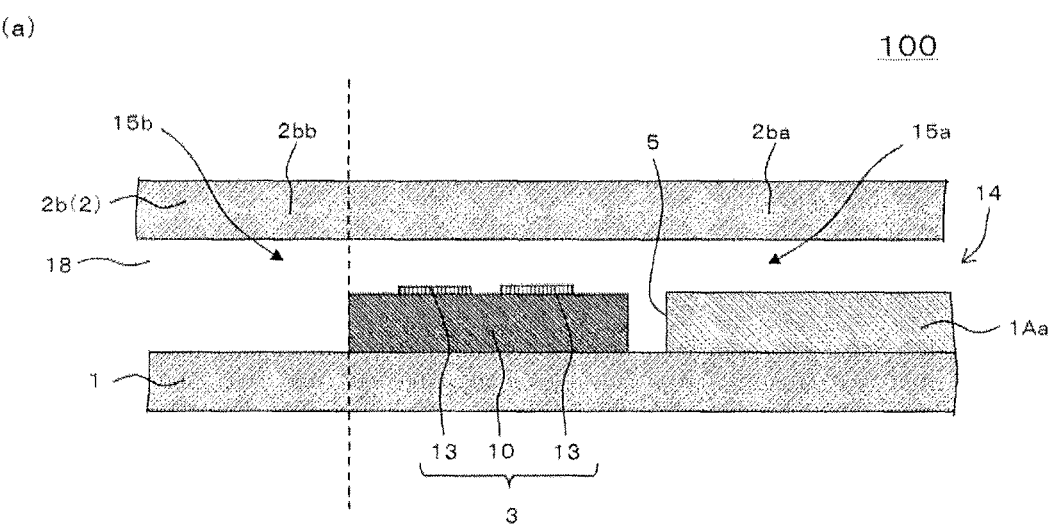
FIG. 5 is a sectional view showing the detecting element of the sensor apparatus shown in FIG. 1.
Figure 5:
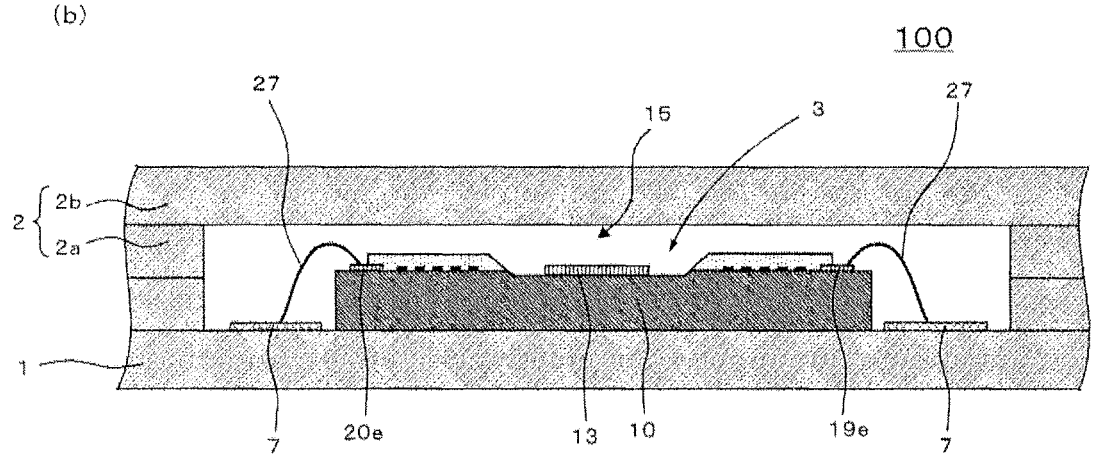

The detecting element 3 in the present embodiment will be described with reference to FIGS. 1 to 6, in particular, FIGS. 4 to 6.

Figure 6:
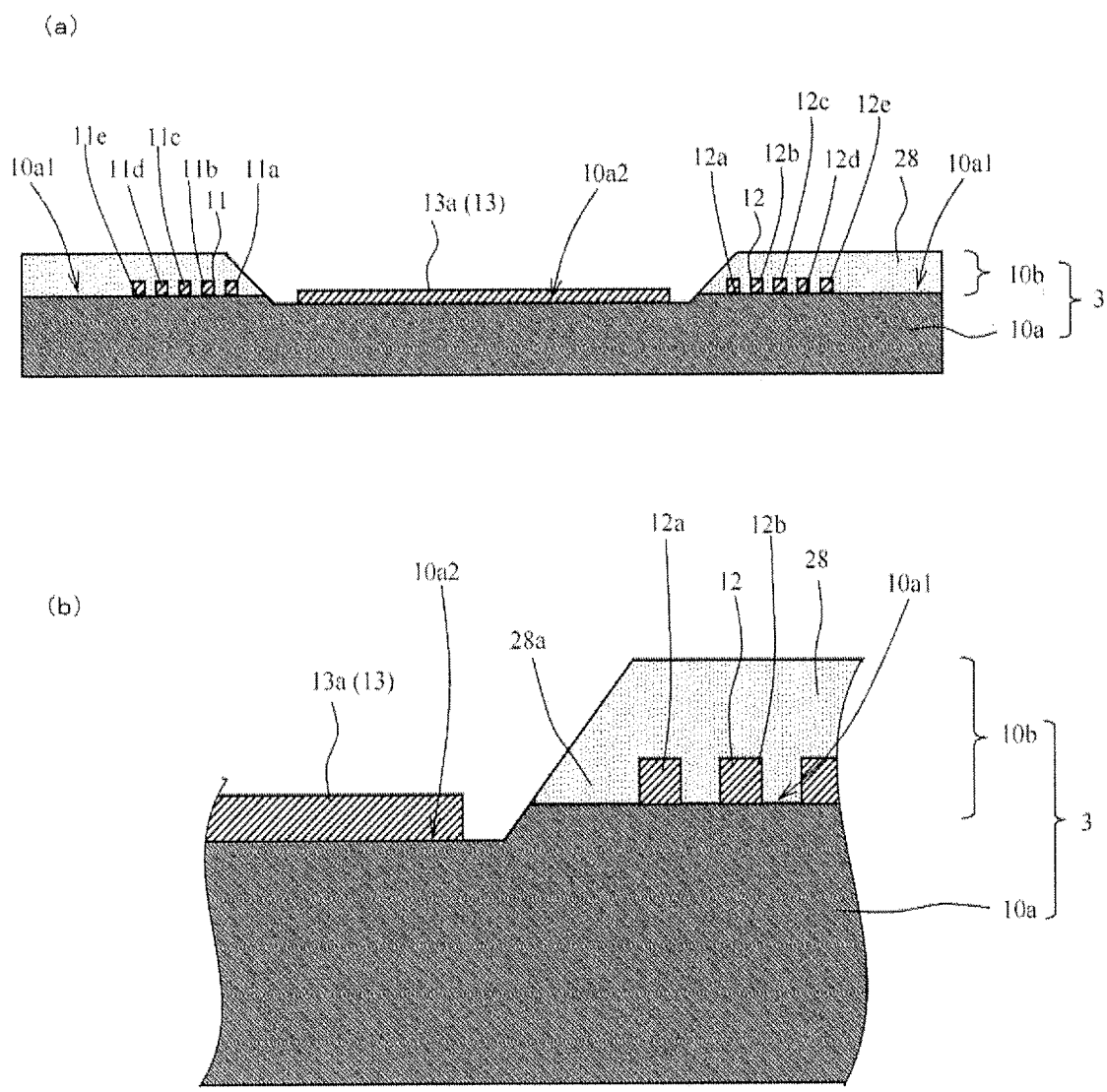
FIG. 6 is an enlarged sectional view showing part of the sensor apparatus shown in FIG. 5.

As shown in FIG. 6, the detecting element 3 generally comprises an element substrate 10a disposed on the upper surface of the first cover member 1, and at least one detecting section 10b, disposed on the upper surface of the element substrate 10a, for detecting an object to be detected (detection target) contained in an analyte liquid.

More specifically, the detecting element 3 in the present embodiment comprises: the element substrate 10a; the detecting section 10b disposed on the upper surface of the element substrate 10a, the detecting section 10b including the reaction section 13 having an immobilization film 13a to detect an object to be detected, a first IDT (InterDigital Transducer) electrode 11 configured to generate an acoustic wave which propagates toward the reaction section 13, and a second IDT electrode 12 configured to receive the acoustic wave which has passed through the reaction section 13; and a protective film 28 which covers the first IDT electrode 11 and the second IDT electrode 12. The upper surface of the element substrate 10a is configured so that a region 10a2 thereof where the reaction section 13 is located is at a lower level than regions 10a1 thereof where the first IDT electrode 11 and the second IDT electrode 12 are located. The detecting section 10b includes, in addition to the first IDT electrode 11, the reaction section 13, and the second IDT electrode 12, the protective film 28, a first extraction electrode 19, a second extraction electrode 20, and so forth. The protective film 28 may be given any shape which is capable of covering the first IDT electrode 11 and the second IDT electrode 12 without limitation. For example, the protective film 28 may cover a region extending from the first IDT electrode 11 to the second IDT electrode 12, or discretely cover the first IDT electrode 11 and the second IDT electrode 12.

(Element Substrate 10a)

The element substrate 10a is constructed of a substrate of single crystal having piezoelectric properties such for example as quartz, lithium tantalate ($LiTaO_3$) single crystal, or lithium niobate ($LiNbO_3$) single crystal. The planar configuration and dimensions of the element substrate 10a are suitably determined. The element substrate 10a has a thickness of 0.3 mm to 1 mm, for example.

In this embodiment, as described above, as shown in FIGS. 6(a) and 6(b), the upper surface of the element substrate 10a is configured so that the region 10a2 where the reaction section 13 is located is at a lower level than the regions 10a1 where the first IDT electrode 11 and the second IDT electrode 12 are located. In this case, in the reaction section 13, energy of SAW (Surface Acoustic Wave) propagating between the first IDT electrode 11 and the second IDT electrode 12 is readily concentrated on the immobilization film 13a, wherefore an object to be detected contained in an analyte liquid can be detected with high sensitivity. In the upper surface of the element substrate 10a, given that the wavelength of SAW propagating between the first IDT electrode 11 and the second IDT electrode 12 is $\lambda$, then the region 10a2 where the reaction section 13 is located is 0.02 $\lambda$ or below lower than the regions 10a1 where the first IDT electrode 11 and the second IDT electrode 12 are located.

The upper surface of the element substrate 10a is configured so that a surface roughness of the region 10a2 where the reaction section 13 is located is greater than a surface roughness of the regions 10a1 where the first IDT electrode 11 and the second IDT electrode 12 are located. In this case, in the reaction section 13, aptamers, antibodies, etc., which will hereafter be described, can be immobilized at high densities, thus achieving an improvement in detection sensitivity. The surface roughness of each constituent element is determined by measurement using arithmetic average roughness Ra. In the case where a film such as an electrode or the like is disposed on the upper surface, which is a measurement target, of the element, for example, graphic analyses of the sectional profile of the upper surface are performed on the basis of a photograph of the section obtained by means of SEM (Scanning Electron Microscopy), TEM (Transmission Electron Microscopy), or otherwise, for surface roughness measurement. Moreover, when direct measurement of the upper surface which is a measurement target is possible, the measurement is effected with use of a commonly-used surface-roughness meter of contact type or non-contact type. The conditions described hold in what follows unless otherwise specified.

A surface roughness of a region of the element substrate 10a where the immobilization film 13a is located is greater than a surface roughness of the upper surface of the immobilization film 13a. This makes it possible to increase the strength of adhesion between the element substrate 10a and the immobilization film 13a, as well as to immobilize aptamers, antibodies, etc. onto the immobilization film 13a at high densities, and thereby achieve an improvement in detection sensitivity.

(IDT Electrodes 11 and 12)

As shown in FIGS. 4 and 6, the first IDT electrode 11 comprises a pair of comb electrodes. Each comb electrode includes two bus bars opposed to each other and a plurality of electrode fingers 11a to 11e (11a, 11b, 11c, 11d) each extending from corresponding one of the bus bars toward the other. A pair of the comb electrodes is disposed so that the plurality of electrode fingers 11a to 11e are arranged in an interdigitated pattern. The second IDT electrode 12 is similar in configuration to the first IDT electrode 11. The first IDT electrode 11 and the second IDT electrode 12 constitute a transversal IDT electrode.

The first IDT electrode 11 is intended for generation of predetermined SAW, and the second IDT electrode 12 is intended for reception of the SAW generated in the first IDT electrode 11. The first IDT electrode 11 and the second IDT electrode 12 are positioned on the same straight line so that the SAW generated in the first IDT electrode 11 can be received by the second IDT electrode 12. Frequency response characteristics can be designed on the basis of the number of the electrode fingers of the first IDT electrode 11 and the second IDT electrode 12, the distance between the adjacent electrode fingers, the crossing width of the electrode fingers, etc., used as parameters.

There are various modes of vibration for SAW to be excited by the IDT electrode. In the detecting element 3 according to the embodiment, for example, a vibration mode of transversal waves called SH waves is utilized. The frequency of SAW may be set within the range of several megahertz (MHz) to several gigahertz (GHz), for example. It is advisable to set the SAW frequency within the range of several hundred MHz to 2 GHz from the practicality standpoint, and also in the interest of miniaturization of the detecting element 3 that will eventually be conducive to miniaturization of the sensor apparatus 100. The thicknesses and lengths of predetermined constituent elements in the embodiment will be described with respect to the case where the center frequency of SAW falls in a several hundred MHz range.

The first IDT electrode 11 and the second IDT electrode 12 may be of a single-layer structure composed of, for example, a gold thin layer, or may be of a multilayer structure such as a three-layer structure composed of a titanium layer, a gold layer, and a titanium layer, or a three-layer structure composed of a chromium layer, a gold layer, and a chromium layer, in the order named, from the element-substrate 10a side.

A thickness of the first IDT electrode 11 and the second IDT electrode 12 may be set to fall within the range of 0.005 λ to 0.015 λ, for example.

An elastic member may be disposed externally of the first IDT electrode 11 and the second IDT electrode 12 in a SAW propagation direction (width direction) to reduce SAW reflection.

(Reaction Section 13)

As shown in FIGS. 4 and 6, the reaction section 13 is disposed between the first IDT electrode 11 and the second IDT electrode 12.

In this embodiment, the reaction section 13 comprises the immobilization film 13a (for example, a metallic film) formed on the upper surface of the element substrate 10a, and a reactant immobilized on the upper surface of the immobilization film 13a for reaction with an object to be detected. The reactant is suitably selected depending on an object to be detected which is a detection target. For example, when the object to be detected is a specific cell or living tissue present in an analyte liquid, an aptamer composed of a nucleic acid or a peptide can be used as the reactant. For example, in this embodiment, while a reaction between the reactant and the object to be detected may be a binding reaction of the object to be detected and the reactant such as a chemical reaction or an antigen-antibody reaction, the reaction is not so limited, but may be a binding reaction of the object to be detected and the reactant under the interaction of the object to be detected with the reactant, or an adsorption reaction of the object to be detected to the reactant. Exemplary of a reactant which can be used for the reaction section 13 in the embodiment is one which causes, by its presence, variation in surface-acoustic-wave characteristics according to the type or content of the object to be detected when an analyte is brought into contact with the reaction section 13. The reaction section 13 is intended for reaction with an object to be detected contained in an analyte liquid, and, more specifically, upon contact of an analyte liquid with the reaction section 13, a specific object to be detected contained in the analyte liquid is bound to an aptamer adapted to the object to be detected.

The immobilization film 13a (metallic film) may be of a single-layer structure composed of, for example, a gold layer, or may be of a multilayer structure such as a two-layer structure composed of a titanium layer and a gold layer situated on the titanium layer or a two-layer structure composed of a chromium layer and a gold layer situated on the chromium layer. Moreover, the immobilization film 13a may be formed of the same material as a material used for the first IDT electrode 11 and the second IDT electrode 12. In this case, the immobilization film 13a and the first and second IDT electrodes 11 and 12 can be formed in the same process step. Instead of the above-mentioned metallic film, for example, an oxide film such as a $SiO_2$ film or $TiO_2$ film may be used as the material of construction of the immobilization film 13a.

Given that the first IDT electrode 11, the second IDT electrode 12, and the reaction section 13 arranged in the width direction of the flow channel are grouped into a set, then, as shown in FIG. 4, two sets are provided in the sensor apparatus 100 according to the embodiment. In this case, by designing the reaction section 13 of one of the sets and the reaction section 13 of the other to undergo reaction with different objects to be detected, it is possible to detect two different objects to be detected by a single sensor apparatus.

In this embodiment, as shown in FIG. 6(b), the upper surface of the immobilization film 13a is positioned at a higher level than at least one of the regions 10a1 of the upper surface of the element substrate 10a where the first IDT electrode 11 and the second IDT electrode 12 are located, respectively. In this case, in the reaction section 13, energy of SAW propagating between the first IDT electrode 11 and the second IDT electrode 12 is readily concentrated on the upper surface of the immobilization film 13a, wherefore an object to be detected can be detected with higher sensitivity.

Moreover, as shown in FIG. 6(b), the upper surface of the immobilization film 13a is positioned at a lower level than at least one of the upper surface of the first IDT electrode 11 and the upper surface of the second IDT electrode 12. In this case, in the reaction section 13, energy of SAW propagating between the first IDT electrode 11 and the second IDT electrode 12 is readily concentrated on the upper surface of the immobilization film 13*a*, wherefore an object to be detected can be detected with higher sensitivity.

A thickness of the immobilization film 13*a* may be set to fall within the range of 0.005 λ to 0.015 λ, for example. In this embodiment, as shown in FIG. 6(*b*), the thickness of the immobilization film 13*a* is smaller than at least one of the thickness of the first IDT electrode 11 and the thickness of the second IDT electrode 12. In this case, even if the immobilization film 13*a* has a relatively small thickness, in the reaction section 13, losses of energy of SAW propagating between the first IDT electrode 11 and the second IDT electrode 12 can be reduced. In addition to that, since the SAW energy is readily concentrated on the upper surface of the immobilization film 13*a*, it is possible to detect an object to be detected with higher sensitivity.

The surface roughness of the upper surface of the immobilization film 13*a* is greater than at least one of the surface roughness of the upper surface of the first IDT electrode 11 and the surface roughness of the upper surface of the second IDT electrode 12. In this case, in the reaction section 13, since an increase in surface area can be achieved, it is possible to immobilize aptamers, antibodies, etc. at high densities, and thereby improve the detection sensitivity even further. The surface roughness of the upper surface of the immobilization film 13*a*, which falls in the range of, for example, 0.5 to 2.0 nm in terms of Ra, may be obtained by measuring the upper surface, as a measurement target, using a commonly-used surface-roughness meter of contact type or non-contact type. Moreover, the surface roughness of the upper surface of each of the first IDT electrode 11 and the second IDT electrode 12 may be obtained by measuring the upper surface, as a measurement target, of either any of comb electrode portions or a portion connecting these electrode portions using a commonly-used surface-roughness meter of contact type or non-contact type.

(Protective Film 28)

As shown in FIG. 6, the protective film 28 covers the first IDT electrode 11 and the second IDT electrode 12. This makes it possible to inhibit an analyte liquid from contact with the first IDT electrode 11 and the second IDT electrode 12, and thereby retard corrosion of the IDT electrodes caused by oxidation, for example. Examples of materials used for the protective film 28 include silicon oxide, aluminum oxide, zinc oxide, titanium oxide, silicon nitride, and silicon. Such a material is properly used as a major constituent, namely a component constituting the greatest proportion in mass, of the protective film 28-forming material, and is therefore not defined as the constituent material when mixed as impurities in very small amounts.

In this embodiment, as shown in FIG. 6(*b*), the protective film 28 lies also in between the reaction section 13 and at least one of the first IDT electrode 11 and the second IDT electrode 12. This interposed portion 28*a* makes it possible to inhibit or reduce contact of the side of the IDT electrode with an analyte liquid. In this construction, as shown in FIG. 6(*b*), the protective film 28 is located without contact with and apart from the reaction section 13. This helps reduce the influence of the protective film 28 upon the sensitivity of the reaction section 13 to SAW.

Moreover, as shown in FIG. 6(*b*), the protective film 28 is configured so that, when viewed in a lateral section thereof, a lower end part of an end located on the reaction section 13 side of the protective film 28 is closer to the reaction section 13 than an upper end part of the end part. As used herein, the language "lateral section" means, as will be seen from FIG. 1(*b*) for example, a section taken along the line a-a of FIG. 1(*a*) or a line perpendicular to the line a-a, looking from the side of the sensor apparatus. Moreover, the language "end located on the reaction section 13 side" means an end of the protective film 28 opposite the end of at least one of the first IDT electrode 11 and the second IDT electrode 12 under the condition where, for example, as described above, the protective film 28 lies also in between the reaction section 13 and at least one of the first IDT electrode 11 and the second IDT electrode 12, and does not cover the entire area of the reaction section 13. Furthermore, as shown in FIG. 6(*b*), in the protective film 28 as viewed in a lateral section, the end located on the reaction section 13 side is inclined so that the distance between the end and the reaction section 13 becomes shorter gradually from the upper end part to the lower end part. This makes it possible to inhibit an analyte liquid from contact with the first IDT electrode 11 and the second IDT electrode 12 more effectively. Moreover, by forming the protective film 28 so as to cover the upper surface of the element substrate 10*a*, it is possible to enhance stability of connection with the element substrate 10*a*.

In this embodiment, a thickness of the protective film 28 may be set to fall within the range of 0.001 λ to 0.05 λ, for example. While the thickness of the protective film 28 may be defined as the distance from the upper surface of the element substrate 10*a* to the upper surface of the protective film 28 as measured in a part of the protective film 28 which covers neither the first IDT electrode 11 nor the second IDT electrode 12, the measurement in other part will not be excluded herein.

A thickness of the protective film 28 may be set to be smaller than at least one of the thickness of the first IDT electrode 11 and the thickness of the second IDT electrode 12. This makes it possible to reduce the influence of the protective film 28 upon SAW propagating between the first IDT electrode 11 and the second IDT electrode 12, and thereby reduce losses of SAW energy. In this case, the upper surface of the protective film 28 may be, at least partly, positioned at a lower level than at least one of the upper surface of the first IDT electrode 11 and the upper surface of the second IDT electrode 12.

As shown in FIGS. 4 and 6, the first IDT electrode 11 and the second IDT electrode 12 include the plurality of electrode fingers 11*a* to 11*e* which are spaced apart from each other and a plurality of electrode fingers 12*a* to 12*e* (12*a*, 12*b*, 12*c*, 12*d*, and 12*e*) which are spaced apart from each other, respectively, and, as shown in FIG. 6(*b*), the protective film 28 is made in continuous (connected) form so as to lie over two adjacent electrode fingers, for example, the electrode fingers 11*a* and 11*b*, as well as 12*a* and 12*b* of the plurality of electrode fingers 11*a* to 11*e*, as well as 12*a* to 12*e*, and also over a part of the element substrate 10*a* which is exposed between the two adjacent electrode fingers 11*a* and 11*b*, as well as 12*a* and 12*b*. This makes it possible to inhibit occurrence of short-circuiting between the plurality of electrode fingers of the IDT electrode caused by an analyte liquid.

(Extraction Electrodes 19 and 20)

As shown in FIG. 4, the first extraction electrode 19 is connected to the first IDT electrode 11, and the second extraction electrode 20 is connected to the second IDT electrode 12. The first extraction electrode 19 is extracted from the first IDT electrode 11 in the opposite direction to the reaction section 13, and, an end 19*e* of the first extraction electrode 19 is electrically connected to the wiring line 7 disposed in the first cover member 1. The second extraction electrode 20 is extracted drawn from the second IDT electrode 12 in the opposite direction to the reaction section 13, and, an end 20e of the second extraction electrode 20 is electrically connected to the wiring line 7.

The first extraction electrode 19 and the second extraction electrode 20 may be made similar in material and configuration to the first IDT electrode 11 and the second IDT electrode 12, and may thus be of a single-layer structure composed of, for example, a gold thin layer, or may be of a multilayer structure such as a three-layer structure composed of a titanium layer, a gold layer, and a titanium layer, or a three-layer structure composed of a chromium layer, a gold layer, and a chromium layer, in the order named, from the element-substrate 10a side.

(Detection of Object to be Detected Using Detecting Element 3)

In the process of detection of an object to be detected contained in an analyte liquid by the detecting element 3 that utilizes SAW as above described, the first step is to apply a predetermined voltage from external measuring equipment to the first IDT electrode 11 via the wiring line 7, the first extraction electrode 19, and so forth.

Upon the voltage application, on the surface of the element substrate 10a, the first IDT electrode 11-forming region 10a1 is excited, thus producing SAW having a predetermined frequency. Part of the SAW so generated propagates toward the reaction section 13, passes through the reaction section 13, and reaches the second IDT electrode 12. In the reaction section 13, the aptamer on the reaction section 13 is bound to a specific object to be detected contained in the analyte liquid under mutual reaction, and the weight (mass) of the reaction section 13 changes correspondingly, which results in variation in the characteristics, such as a phase, of the SAW passing through the reaction section 13. In response to the arrival of the SAW having varied characteristics at the second IDT electrode 12, a corresponding voltage is developed in the second IDT electrode 12.

The thereby developed voltage is outputted through the second extraction electrode 20, the wiring line 70, and so forth. By reading the output with external measuring equipment, it is possible to examine the properties and constituents of the analyte liquid containing the object to be detected.

In the sensor apparatus 100, capillarity is utilized to direct the analyte liquid to the reaction section 13. Specifically, as described earlier, when the second cover member 2 is joined to the intermediate cover member 1A, as shown in FIG. 1, the flow channel 15 is defined, in the form of a narrow elongate pipe, on the lower surface of the second cover member 2. Thus, by setting, for example, the width or the diameter of the flow channel 15 at a predetermined value with consideration given to the type of the analyte liquid, the materials of construction of the intermediate cover member 1A and the second cover member 2, and so forth, it is possible to cause capillarity in the flow channel 15 in the form of a narrow elongate pipe. For example, the flow channel 15 has a width of 0.5 mm to 3 mm, and a depth of 0.1 mm to 0.5 mm. As shown in FIG. 1(b), the flow channel 15 has a downstream portion (extension) 15b which is a portion extending beyond the reaction section 13, and, the second cover member 2 is formed with the air release hole 18 which is in communication with the extension 15b. Upon admission of the analyte liquid into the flow channel 15, air present in the flow channel 15 is expelled out of the air release hole 18.

With such a pipe form capable of causing capillarity defined by the cover members including the intermediate cover member 1A and the second cover member 2, upon contact with the inlet port 14, the analyte liquid is drawn into the interior of the sensor apparatus 100 while passing through the flow channel 15. Thus, the sensor apparatus 100 has an analyte liquid suction mechanism built in itself, and is therefore capable of analyte liquid suction without using an instrument such as a pipette.

(Positional Relationship Between Flow Channel 15 and Detecting Element 3)

In this embodiment, while the analyte-liquid flow channel 15 has a depth of about 0.3 mm, the detecting element 3 has a thickness of about 0.3 mm, that is; as shown in FIG. 1(b), the depth of the flow channel 15 and the thickness of the detecting element 3 are substantially equal. Therefore, if the detecting element 3 is placed as it is on the upper surface of the first cover member 1, the flow channel 15 will be blocked. In this regard, in the sensor apparatus 100, as shown in FIGS. 1(b) and 5, the element placement section 5 is defined by the first cover member 1 on which the detecting element 3 is mounted, and the intermediate cover member 1A joined onto the first cover member 1. The detecting element 3 is housed in this element placement section 5 so that the analyte-liquid flow channel 15 will not be blocked. That is, the depth of the element placement section 5 is adjusted to be substantially equal to the thickness of the detecting element 3, and, the detecting element 3 is mounted inside the element placement section 5. Thereby, the flow channel 15 can be provided.

The detecting element 3 is secured to the bottom surface of the element placement section 5 by, for example, a die-bonding material composed predominantly of resin such as epoxy resin, polyimide resin, or silicone resin.

The end 19e of the first extraction electrode 19 and the wiring line 7 are electrically connected to each other by a metallic narrow wire 27 formed of, for example, Au. The connection between the end 20e of the second extraction electrode 20 and the wiring line 7 is made in a similar way. Means for connecting the wiring line 7 with the first and second extraction electrodes 19 and 20 is not limited to the metallic narrow wire 27, but may be of an electrically-conductive adhesive such as a Ag paste. Since a gap is left in the part where the wiring line 7 makes connection with each of the first and second extraction electrodes 19 and 20, it is possible to suppress damage of the metallic narrow wire 27 when bonding the second cover member 2 to the first cover member 1. Moreover, the first extraction electrode 19, the second extraction electrode 20, the metallic narrow wire 27, and the wiring line 7 are covered with the protective film 28. By covering the first extraction electrode 19, the second extraction electrode 20, the metallic narrow wire 27, and the wiring line 7 with the protective film 28, it is possible to suppress corrosion of these electrodes and the like.

As described heretofore, according to the sensor apparatus 100 in the embodiment, by placing the detecting element 3 in the element placement section 5 of the first cover member 1, it is possible to provide the analyte-liquid flow channel 15 extending from the inlet port 14 to the reaction section 13, and thereby allow the analyte liquid, which has been drawn into the apparatus through the inlet port 14 under capillarity for example, to flow to the reaction section 13. That is, even with use of the detecting element 3 having a certain thickness, since the sensor apparatus 100 has an analyte liquid suction mechanism built in itself, it is possible to provide a sensor apparatus 100 capable of directing an analyte liquid to the detecting element 3 efficiently.

<Manufacturing Process of Detecting Element>

Figure 7:
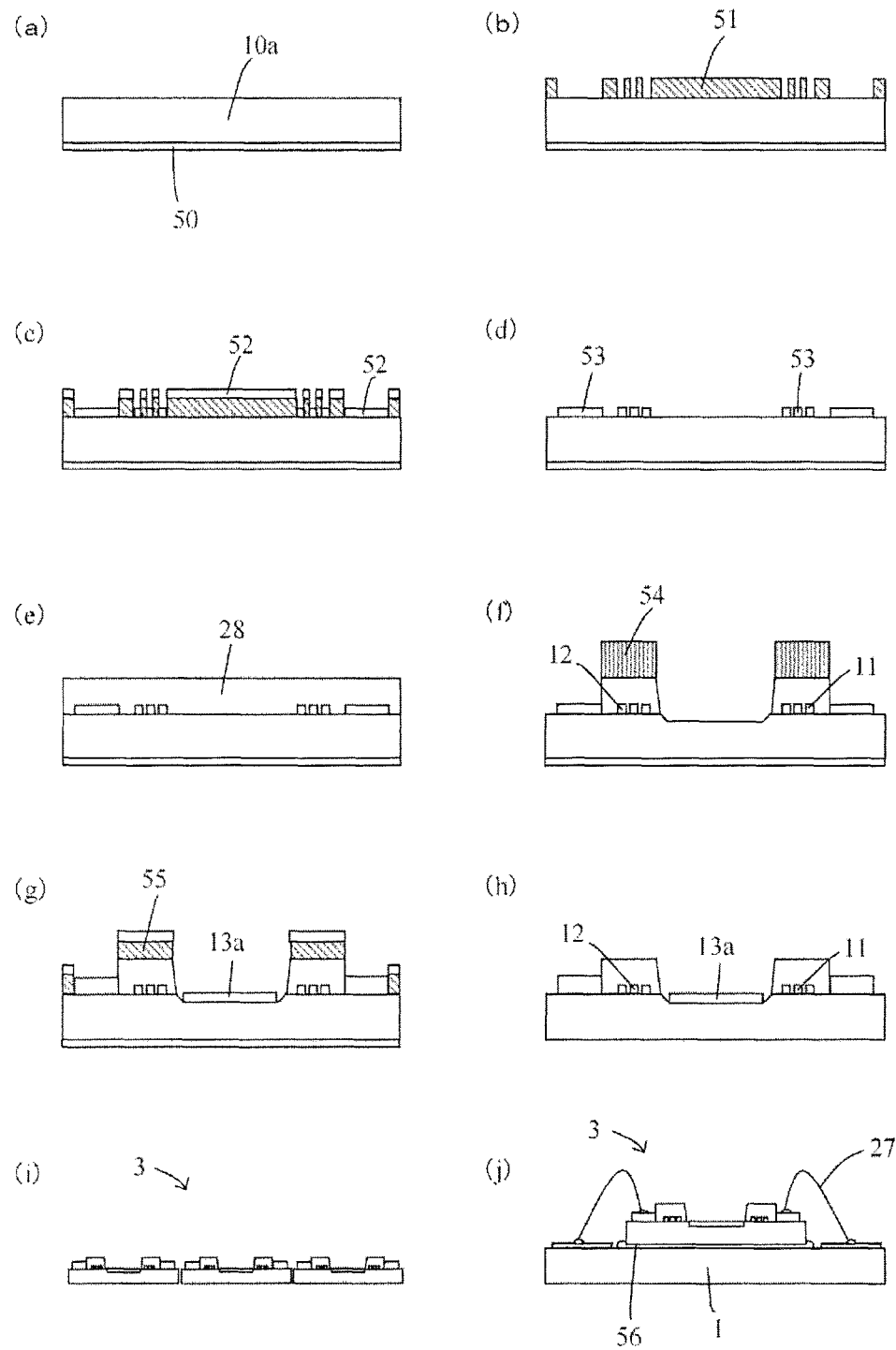
FIG. 7 is a schematic view showing procedural steps to manufacture the detecting element 3.

The following describes a procedure in the making of the detecting element 3 provided in the sensor apparatus 100 according to the embodiment of the invention. FIG. 7 is a schematic view showing procedural steps for manufacturing the detecting element 3.

First, a quartz-made element substrate 10a is washed. After that, on an as needed basis, an Al film is formed on the lower surface of the element substrate 10a by RF sputtering technique (FIG. 7(a)).

Next, an electrode pattern is formed on the upper surface of the element substrate 10a. In this step, a photoresist pattern 51 of image reversal type for electrode-pattern formation is formed by photolithography technique (FIG. 7(b)).

Next, a metallic layer 52 having a three-layer structure composed of Ti/Au/Ti layers is formed on each of a photoresist-bearing part and a photoresist-free part of the upper surface of the element substrate 10a by electron-beam vapor deposition equipment (FIG. 7(c)).

Next, a Ti/Au/Ti electrode pattern 53 is formed by lifting off the photoresist pattern 51 using a solvent, followed by oxygen-plasma ashing treatment (FIG. 7(d)). In this embodiment, the Ti/Au/Ti electrode pattern 53 constitutes, in addition to a pair of IDT electrodes 11 and 12, a reflector and mounting extraction electrodes 19 and 20. The pair of IDT electrodes 11 and 12 are disposed so as to face each other, and, one of them serves as a transmitter, whereas the other serves as a receiver.

Next, a protective film 28 is formed on the upper surface of the element substrate 10a so as to cover the Ti/Au/Ti electrode pattern by, for example, TEOS (Tetra Ethyl Ortho Silicate)-plasma CVD technique (FIG. 7(e)).

Next, a protective film 28 pattern is formed by forming a positive photoresist 54 on the upper surface of the protective film 28, followed by etching of the protective film 28 using RIE equipment (FIG. 7(f)). At this time, the protective film 28 is overetched at its area corresponding to the center of the element substrate 10a where an immobilization film 13a is to be formed, thus forming a recessed area which is lower in level than nearby area. After that, the photoresist 54 is lifted off with use of a solvent, whereupon the protective film 28 pattern is formed so as to cover the IDT electrodes 11 and 12.

Next, a photoresist pattern 55 for immobilization-film 13a formation is formed by photolithography technique, and a metallic layer having a two-layer structure composed of Au/Ti layers, which becomes a reaction section 13, is formed by electron-beam vapor deposition equipment (FIG. 7(g)). Following the lifting-off of the photoresist pattern 55 using a solvent, oxygen-plasma ashing treatment is performed, whereupon the immobilization film 13a having a two-layer structure composed of Au/Ti layers is formed so as to lie between the paired IDT electrodes 11 and 12 (FIG. 7(h)). Given that the pair of IDT electrodes 11 and 12 and the Au/Ti immobilization film 13a are grouped into a set, then two sets are provided on a single sensor. One of the two sets is used as a set for detection, whereas the other is used as a set for reference. After that, the Al film 50 formed on the lower surface of the element substrate 10a is removed with use of fluonitric acid.

An aptamer composed of a nucleic acid or a peptide is immobilized on the upper surface of the immobilization film 13a to form the reaction section 13.

In the manner as described heretofore, the detecting element 3 is formed.

Next, the element substrate 10a is cut in a predetermined size by dicing (FIG. 7(i)). After that, separate detecting elements 3 obtained by cutting process are fixedly attached, at their back sides, onto a glass epoxy mounting substrate having a wiring formed thereon in advance (hereafter referred to as "mounting substrate") which is equivalent to the first cover member 1, with use of an epoxy adhesive. Then, a Au narrow wire used as the lead wire 27 is set to provide electrical connection between the wiring line 7 connected to each of the terminals 6 disposed on the mounting substrate and each of the ends 19e and 20e of the extraction electrodes disposed on the detecting element 3 (FIG. 7(j)).

Following the completion of placement of the intermediate cover member 1A, the second cover member 2, and so forth, the sensor apparatus 100 is formed.

The manufacturing process of the detecting element 3, as well as the manufacturing process of the sensor apparatus 100, is not limited to the aforestated procedure shown in FIG. 7, and it is thus possible to adopt any other manufacturing process that enables production of the element substrate 10a whose upper surface is configured so that the region 10a2 where the reaction section 13 is located is lower than the regions 10a1 where the first IDT electrode 11 and the second IDT electrode 12 are located.

The invention is not limited to the embodiment thus far described, and may therefore be carried into effect in various forms.

Although the reaction section 13 in the aforestated embodiment has been illustrated as comprising the immobilization film 13a and the aptamer immobilized on the upper surface of the immobilization film 13a, the invention is not limited to the aptamer, and thus, as an alternative, a reactant which undergoes reaction with a object to be detected contained in an analyte liquid and causes variation in SAW characteristics before and after analyte passage through the reaction section 13 may be immobilized on the upper surface of the immobilization film 13a. Moreover, for example, in the case where the object to be detected in the analyte liquid reacts with the immobilization film 13a, the reaction section 13 may be composed solely of the immobilization film 13a without using a reactant such as the aptamer. In addition, the reaction section 13 may be defined by a region between the first IDT electrode 11 and the second IDT electrode 12 on the surface of the element substrate 10a constructed of a piezoelectric substrate without using the immobilization film 13a. In this case, an analyte liquid is applied directly to the surface of the element substrate 10a to detect the physical properties, such as the viscosity, of the analyte liquid. More specifically, SAW phase variation resulting from a change in, for example, the viscosity of the analyte liquid on the reaction section 13 is monitored. Moreover, the aptamer may be immobilized on the upper surface of a non-conductive film which is used as the immobilization film 13a instead of a metallic film.

Moreover, the detecting element 3 may be constructed of a single substrate on which a variety of devices are disposed. For example, an enzyme electrode for use with enzyme electrode method may be disposed next to a SAW device. In this case, in addition to measurement based on the immuno method using an antibody or aptamer, measurement based on the enzymatic method can also be conducted, thus increasing the number of measurement points that can be checked at one time.

Moreover, while the embodiment has been described with respect to the case of providing a single detecting element 3, a plurality of detecting elements 3 may be provided. In this case, the element placement section 5 is formed for each detecting element 3 on an individual basis, or, the element placement section 5 is configured to have a length or width large enough to receive all of the detecting elements 3.

Moreover, while the embodiment has been described with respect to the case where the first cover member 1, the intermediate cover member 1A, and the second cover member 2 are provided as separate components, this does not constitute any limitation, and thus either a combination of some of these members in an unitary structure or a combination of all the members in an unitary structure may be adopted.

REFERENCE SIGNS LIST

1: First cover member
1A: Intermediate cover member
1Aa: First upstream portion
2: Second cover member
2a: Third substrate
2b: Fourth substrate
3: Detecting element
4: Recess-forming area
5: Element placement section
6: Terminal
7: Wiring line
9: Filler member
10a: Element substrate
10b: Detecting section
11: First IDT electrode
12: Second IDT electrode
13: Reaction section
13a: Immobilization film
14: Inlet port
15: Flow channel
15a: Upstream portion
15b: Downstream portion (extension)
18: Air release hole
19: First extraction electrode
19e: End
20: Second extraction electrode
20e: End
27: Lead wire (metallic narrow wire)
28: Protective film
100: Sensor apparatus

The invention claimed is:

1. A sensor apparatus, comprising:
an element substrate comprising a first top surface, a second top surface and a third top surface;
a detecting section disposed on the first top surface of the element substrate, the detecting section comprising a reaction section having an immobilization film disposed on and directly contacting the first top surface, wherein the immobilization film is configured to detect an object to be detected, a first IDT electrode disposed on the second top surface of the element substrate and configured to generate an acoustic wave which propagates toward the reaction section, and a second IDT electrode disposed on and contacting the third top surface of the element substrate and configured to receive the acoustic wave which has passed through the reaction section; and
a protective film which covers the first IDT electrode and the second IDT electrode,
wherein the first top surface of the element substrate is at a lower level than the second and third top surfaces of the element substrate.

2. The sensor apparatus according to claim 1,
wherein an upper surface of the immobilization film is positioned at a higher level than the second and third top surfaces of the element substrate.

3. The sensor apparatus according to claim 1,
wherein an upper surface of the immobilization film is positioned at a lower level than at least one of an upper surface of the first IDT electrode and an upper surface of the second IDT electrode.

4. The sensor apparatus according to claim 3,
wherein a material for the immobilization film is the same as a material for the first IDT electrode and the second IDT electrode.

5. The sensor apparatus according to claim 1,
wherein a thickness of the immobilization film is smaller than at least one of a thickness of the first IDT electrode and a thickness of the second IDT electrode.

6. The sensor apparatus according to claim 1,
wherein a surface roughness of an upper surface of the immobilization film is greater than at least one of a surface roughness of an upper surface of the first IDT electrode and a surface roughness of an upper surface of the second IDT electrode.

7. The sensor apparatus according to claim 1, wherein a surface roughness of the first top surface of the element substrate is greater than a surface roughness of the second top surface of the element substrate and the third top surface of the element substrate.

8. The sensor apparatus according to claim 1,
wherein a surface roughness of the first top surface of the element substrate is greater than a surface roughness of an upper surface of the immobilization film.

9. The sensor apparatus according to claim 1,
wherein the protective film is located between the reaction section and at least one of the first IDT electrode and the second IDT electrode.

10. The sensor apparatus according to claim 1,
wherein the protective film is spaced away from the reaction section.

11. The sensor apparatus according to claim 1,
wherein an end of the protective film located on a side of the reaction section comprises a lower end part and an upper end part, the lower end part being closer to the immobilization film than the upper end part when viewed in a lateral section.

12. The sensor apparatus according to claim 1,
wherein an end of the protective film located on a side of the reaction section comprises a lower end part and a upper end part, the end being inclined so that a distance between the end and the immobilization film becomes shorter as the end going from the upper end part to the lower end part when viewed in a lateral section.

13. The sensor apparatus according to claim 1,
wherein a thickness of the protective film is smaller than at least one of a thickness of the first IDT electrode and a thickness of the second IDT electrode.

14. The sensor apparatus according to claim 1, wherein each of the first IDT electrode and the second IDT electrode comprises a plurality of comb electrodes which are spaced apart from each other, and
the protective film lies over two adjacent comb electrodes of the plurality of comb electrodes and a part of the element substrate which is exposed between the two adjacent comb electrodes.

15. The sensor apparatus according to claim 1,
wherein the protective film comprises silicon oxide.

16. The sensor apparatus according to claim 1,
wherein the immobilization film comprises a metallic film located on the first top surface of the element substrate.

17. The sensor apparatus according to claim 1,
wherein the immobilization film comprises an oxide film located on the first top surface of the element substrate.

* * * * *